(12) United States Patent
Lattimore, Jr. et al.

(10) Patent No.: US 9,630,888 B1
(45) Date of Patent: Apr. 25, 2017

(54) SANITARY WASTE TREATMENT METHOD

(71) Applicant: B.A.M.2 Waste Water Consulting, Ptr., Springfield, TN (US)

(72) Inventors: Sidney Lattimore, Jr., Macon, GA (US); Buford Harold Denton Summers, III, Dresden, TN (US)

(73) Assignee: B.A.M.2 Waste Water Consulting, Ptr., Springfield, TN (US)

( * ) Notice: Subject to any disclaimer, the term of this patent is extended or adjusted under 35 U.S.C. 154(b) by 0 days.

(21) Appl. No.: 15/156,985

(22) Filed: May 17, 2016

(51) Int. Cl.
*B09B 3/00* (2006.01)
*C05F 3/00* (2006.01)
*C05F 3/04* (2006.01)
*A61L 2/18* (2006.01)

(52) U.S. Cl.
CPC ............... *C05F 3/00* (2013.01); *C05F 3/04* (2013.01); *A61L 2/18* (2013.01)

(58) Field of Classification Search
CPC ... A62D 2101/22; A62D 2101/28; B09B 3/00
USPC .................................. 588/313, 405
See application file for complete search history.

(56) References Cited

U.S. PATENT DOCUMENTS

| | | |
|---|---|---|
| 3,915,853 A | 10/1975 | Luck |
| 5,240,600 A | 8/1993 | Wang et al. |
| 6,146,531 A | 11/2000 | Matheson |
| 7,481,940 B2 | 1/2009 | Clifford, III et al. |
| 7,566,400 B2 | 7/2009 | Harmon et al. |
| 7,727,397 B2 | 6/2010 | Gerardi et al. |
| 8,192,626 B2 | 6/2012 | Theodore et al. |
| 8,597,513 B2 | 12/2013 | Borole et al. |
| 2013/0193068 A1 | 8/2013 | Jones et al. |
| 2014/0116938 A1 | 5/2014 | Theodore |
| 2014/0124438 A1 | 5/2014 | Anker et al. |

FOREIGN PATENT DOCUMENTS

| | | |
|---|---|---|
| CN | 102557274 A | 7/2012 |
| CN | 203124392 U | 8/2013 |
| WO | WO 90/15028 A1 | 12/1990 |

*Primary Examiner* — Edward Johnson
(74) *Attorney, Agent, or Firm* — Frost Brown Todd LLC

(57) ABSTRACT

A sanitary waste treatment method includes the steps of: adding water to sanitary waste to form a slurry characterized by a first biochemical oxygen demand, aerating the slurry, chlorinating the slurry to produce a sterilized slurry, dechlorinating the sterilized slurry to produce a dechlorinated slurry and inoculating the dechlorinated slurry with aerobic bacteria, wherein the aerobic bacteria digest solid waste in the slurry. The sanitary waste treatment method may be utilized in agricultural or municipal settings.

20 Claims, 1 Drawing Sheet

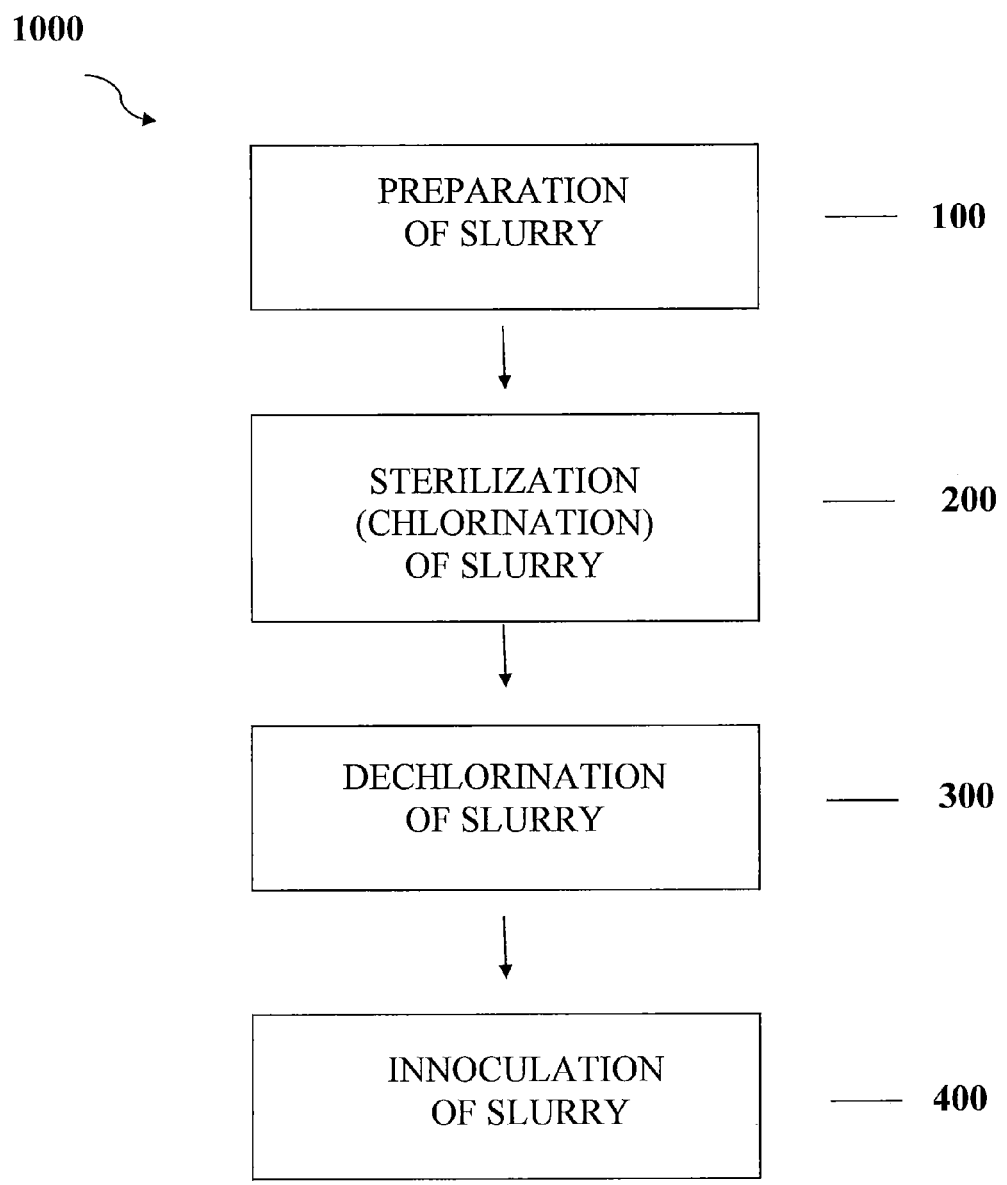

SANITARY WASTE TREATMENT METHOD

Given that a single lactating cow can produce up to 150 pounds of manure per day, a farmer's stockpile of manure may quickly become unmanageable. Yet in small doses, manure may be the stuff of life, i.e., it may serve as the fertilizer that plants need to grow. In light of the foregoing, many farmers spread untreated manure onto fields where their crops are grown. However, the stockpiling of untreated manure, and/or the treatment of fields with untreated manure, may lead to a number of problems including promoting algae blooms, promoting propagation of *salmonella* and *E. Coli*, contamination of groundwater and generation of methane and associated bad odors.

Although anaerobic microbes are commonly used to oxidize the organic constituents in animal or human waste, some have attempted to avoid the aforementioned problems by treating collected manure aerobically. In the aerobic manure treatment process, aerobic microorganisms that are already present in the manure oxidize bio-available organic and nitrogenous compounds, resulting in reduced odor and ammonia emissions. However, aerobic treatment is not widely utilized for the treatment of slurry manure primarily due to the costs associated with operating the motors, compressors or fans required to supply enough oxygen to support the aerobic bacteria.

Sterilization is often one of the last steps in the tertiary treatment of water containing human waste. The purpose of the sterilization step is to substantially reduce the number of microorganisms in the water, which is to be discharged back into the environment for the later use of bathing, drinking, irrigation, etc.

Chlorination is the most common form of waste water sterilization in North America. However, disadvantages of chlorination at the end of waste water treatment may include chlorination of residual organic material, which can generate chlorinated-organic compounds that may be carcinogenic or harmful to the environment. Moreover, residual chlorine or chloramines may also be capable of chlorinating organic material in the natural aquatic environment. Further, because residual chlorine may be toxic to aquatic species, the treated effluent must also be chemically dechlorinated, adding to the complexity and cost of treatment.

While a variety of sanitary waste treatment methods have been devised and utilized in agricultural and municipal settings, it is believed that no one prior to the inventor(s) has devised or used a sanitary waste treatment method as described herein, which surprisingly comprises seemingly disparate and/or disadvantageous steps to decontaminate the sanitary waste so that is suitable for re-use or disposal.

BACKGROUND

The disclosed method comprises seemingly disparate and/or disadvantageous steps of sterilizing the sanitary waste and then re-introducing aerobic bacteria; these steps are seemingly disparate and/or disadvantageous for at least the following reasons. First, sterilization of sanitary waste kills all microbes (including microbial spores) whether they are harmful or helpful to decontaminating the sanitary waste (e.g., anaerobic and aerobic bacteria). Second, by killing all microbes, further contaminants are released into the sanitary waste, including organic compounds and nitrogen. Third, by inoculating sterilized sanitary waste with aerobic bacteria, one would expect to incur significant costs associated with sufficiently aerating the sanitary waste so that the added aerobic bacteria are effective. Fourth, sterilization through chlorination may generate undesired byproducts.

Despite the foregoing, the inventors have surprisingly found that by combining the steps of sterilization and inoculation with aerobic bacteria, that a simple, effective and inexpensive method of decontaminating sanitary waste is achieved. Moreover, the method may be utilized in agricultural settings as well as in municipal sanitary waste treatment systems.

BRIEF DESCRIPTION

The present disclosure describes a method of treating sanitary waste. In some embodiments, the method comprises the steps of: a. adding water to the sanitary waste to form a slurry characterized by a first biochemical oxygen demand; b. aerating the slurry; c. chlorinating the slurry to produce a sterilized slurry; d. dechlorinating the sterilized slurry to produce a dechlorinated slurry; and e. inoculating the dechlorinated slurry with aerobic bacteria, wherein the aerobic bacteria digest the sanitary waste in the slurry. The method may further comprise the steps of separating the slurry into undigested solids and effluent. The effluent may be characterized by a second biochemical oxygen demand that is at least about 50%, or at least about 80%, less than that of the first biochemical oxygen demand. During steps a through e, the pH of the slurry may be: adjusted and/or maintained at pH of from about 6.5 to about 8.0; aerated; stirred; and combinations thereof. In some embodiments, the step of chlorinating the slurry may kill at least about 50% of the microbes contained in the slurry.

In some embodiments, a method of treating sanitary waste comprises the steps of: a. sterilizing a slurry containing the sanitary waste by adding chlorine to the slurry until the slurry has total chlorine residuals of at least about 1.5 parts per million; b. dechlorinating the slurry by adding a sulfur containing compound to the slurry; c. inoculating the slurry with aerobic bacteria; d. digesting solid waste in the slurry with the bacteria; e. aerating the slurry during steps a through d; and f. separating the slurry into undigested solid waste and effluent. In some embodiments, the method may reduce the biochemical oxygen demand of the slurry by at least about 50%, or at least about 80%. In some embodiments, the chlorine is added to the slurry at a concentration of at least about 5 parts per million (hereinafter, "ppm"), or at least about 10 ppm. In some embodiments, the method may further comprise the step of forming the slurry by adding water to sanitary waste; the slurry may have a total liquid content of from about 75% to about 95%. In some embodiments, aerating the slurry may be accomplished using: an impeller aerator, a venturi pump, a vertical aerator and combinations thereof.

In some embodiments, the method comprises the steps of: a. placing slurry comprising sanitary waste and water in a holding receptacle; b. sterilizing the slurry by at least about 95% by adding chlorine to the slurry; c. moving the sterilized slurry into a dechlorination receptacle; d. dechlorinating the slurry by adding a sulfur containing compound to the slurry; e. moving the dechlorinated slurry into a biological receptacle; f. inoculating the slurry with aerobic bacteria; g. digesting solid waste in the slurry with the aerobic bacteria; h. separating the slurry into undigested solid waste and supernatant; i. aerating the slurry during steps b, d, f and g; and in some embodiments, maintaining the slurry at a pH of about 6.5 and about 8.0 during steps b through h.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawing, in which like reference numerals identify the same elements and in which:

FIG. 1 is a schematic diagram showing the steps in a method of treating sanitary waste according to the disclosure.

The drawing is not intended to be limiting in any way, and it is contemplated that various embodiments of the method may be carried out in a variety of other ways, including those not necessarily depicted in the drawing. The accompanying drawing is incorporated in and forms a part of the specification, and illustrates several aspects of the present method, and together with the description serve to explain the principles of the method; it being understood, however, that this method is not limited to the precise arrangements shown.

DETAILED DESCRIPTION

All percentages, ratios and proportions used herein are by weight percent of the composition, unless otherwise specified. All average values are calculated "by weight" of the composition or components thereof, unless otherwise expressly indicated.

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawing and descriptions should be regarded as illustrative in nature and not restrictive.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." All numerical ranges disclosed herein are inclusive and combinable.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Having shown and described various embodiments of the present method, further adaptations of the methods and systems described herein may be accomplished by appropriate modifications by one of ordinary skill in the art without departing from the scope of the present method. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present method should be considered in terms of the following claims and is understood not to be limited to the details of structure and operation shown and described in the specification and drawings.

"Biological receptacle" as used herein means any receptacle that will sufficiently contain sanitary waste before, after or during, treatment of the sanitary waste with biological agents, e.g., microbes, enzymes, etc. Non-limiting examples of biological receptacles include: lagoons, tanks, retention ponds and the like.

"Chlorination receptacle" as used herein means any receptacle that will sufficiently contain sanitary waste before, after or during, chlorination of the sanitary waste. Non-limiting examples of chlorination receptacles include: lagoons, tanks, retention ponds and the like.

"Dechlorination receptacle" as used herein means any receptacle that will sufficiently contain sanitary waste before, after or during, dechlorination of the sanitary waste. Non-limiting examples of dechlorination receptacles include: lagoons, tanks, retention ponds and the like.

"Holding receptacle" as used herein means any receptacle that will sufficiently contain sanitary waste before, after or during, a sanitary waste treatment step. Non-limiting examples of holding receptacles include: lagoons, tanks, retention ponds and the like.

"Sanitary waste" as used herein means waste excreted by an animal or human and may include solid matter, urine and combinations thereof.

"Slurry" as used herein means a suspension of sanitary waste in a liquid, e.g., water.

"Sterilization" as used herein means a process that destroys and/or inactivates microbes by a chemical and/or physical means. "Sterilization" as used herein encompasses partial sterilization or total sterilization.

"Sterilized" as used herein describes destroyed and/or inactivated microbes. "Sterilized" as used herein encompasses the terms "partially sterilized" or "totally sterilized."

The methods described herein may comprise, consist of or consist essentially of the following steps, elements, formulations and other features as set forth in the present disclosure, as well as any additional or optional steps, elements, formulations and other features described herein or that are otherwise useful in relation to the aforementioned methods.

Referencing FIG. 1, in some embodiments, the method (1000) may comprise the following steps:

I. Preparation of Slurry

Referencing FIG. 1, Step 1 (100), if the sanitary waste that is collected and is to be treated is not already in the form of a slurry, liquid, preferably water, may be added to the sanitary waste and mixed to form a slurry. In some embodiments, the slurry may comprise from about 50% to about 95%, from about 60% to about 95% or from about 75% to about 95% liquid. In some embodiments, the slurry may comprise about 50% liquid, about 60% liquid, about 75% liquid, or about 95% liquid. In some embodiments, the slurry may be stored or made when it is present in a holding receptacle.

In some embodiments, it may be desirable for the slurry to have a pH of from about 6.5 to about 8.0. In these embodiments, if the pH of the slurry is not already at a pH of from about 6.5 and about 8.0, it may be adjusted using methods known to those of skill in the art. In some embodiments, the slurry may have, or be adjusted to have, a pH of about 6.5, a pH of about 7.0 or a pH of about 8.0.

The slurry may be characterized by a biochemical oxygen demand (hereinafter, "BOD"), which may be measured using EPA Standard Method 5210 B, i.e., the "5-Day BOD Test," which is incorporated herein by reference. BOD values may be expressed in milligrams of oxygen consumed per liter of sample ("mg/L") during 5 days of incubation at 20° C.

The first or "initial" BOD of a slurry may vary depending upon the source of the sanitary sewage. For example, a slurry comprising human sanitary waste may have a first BOD of at least about 100 mg/L, at least about 200 mg/L, at least about 300 mg/L, at least about 400 mg/L or at least about 500 mg/L. In a further example, a slurry comprising livestock sanitary waste may have a first BOD value that is substantially higher, e.g., at least about 2,000 mg/L, at least about 3,500 mg/L or at least about 5,000 mg/L.

II. Sterilization of the Slurry

Referencing FIG. 1, Step 2 (200), in some embodiments, the slurry is sterilized in order to kill and/or inactivate any microbes in the slurry. Such microbes may include, but are not limited to: bacteria, viruses, parasites, fungi, protista, archae, plants (e.g., algae) and combinations thereof. Without wishing to be bound by theory, it is believed that sterilization of the slurry kills microbes present in the slurry, which may in turn result in their breakdown and release of their organic constituents into the slurry. The organic constituents may then serve as food for living microorganisms that remain viable in the sterilized slurry, and/or are later added to the sterilized slurry.

In some embodiments, sterilization of the slurry may be quantified by one skilled in the art based by measuring the percentage of microbes killed in a given sample. In some embodiments, the sterilization may be quantified via a direct microscopic count (DMC) method.

In some embodiments, the slurry is sterilized, meaning that from about 50% to about 100% of the microbes are destroyed or inactivated. In some embodiments, the slurry may be sterilized by at least about 50%, at least about 60%, at least about 70%, at least about 80%, at least about 90%, at least about 95%, at least about 98%, at least about 99% sterilized, or about 100% sterilized. In some embodiments, it is preferred to sterilize the slurry by at least about 95%.

The slurry may be sterilized using one or more methods known to those of skill in the art. In some embodiments, the slurry may be sterilized through: chlorination, ozonation, exposure to ultraviolet radiation, microfiltration and combinations thereof.

It may be preferable to sterilize the slurry via chlorination, particularly in agricultural settings. The slurry to be chlorinated may remain in the holding receptacle or may be transferred to a chlorination receptacle, such as via gravity feed and/or pumped.

The slurry may be chlorinated by adding a chlorine containing compound to the slurry until the chlorine breakpoint is met, i.e., when the total chlorine residuals in a sample of the slurry is at least about 1.5 ppm, or at least about 2.0 ppm. Chlorine containing compounds may be added to the slurry in gas, liquid and/or solid form. Useful chlorine containing compounds may be selected from the group consisting of the following commercially available compounds: calcium hypochlorite, sodium hypochlorite and combinations thereof.

To sterilize the slurry via chlorination, the slurry may be treated with one or more doses of the chlorine containing compound. For example, as described below, chlorinating the slurry may begin with the addition of a first dose of a chlorine containing compound to the slurry, and after a given time period, measuring a sample of the slurry for total chlorine residuals to determine whether the chlorine breakpoint has been met.

In some embodiments for example, a first dose of at least about 5 ppm, at least about 8 ppm, or at least about 10 ppm of a chlorine containing compound may be added to the slurry, which may be aerated. In some embodiments, aerating the slurry may be accomplished using: an impeller aerator, a venturi pump, a vertical aerator and combinations thereof.

In circumstances in which the sanitary waste to be sterilized has already been treated with a chlorine containing substance in order to reduce odor, a smaller first dose of a chlorine containing compound may suffice. In any case, once the slurry has been chlorinated, in some embodiments, it may be desirable to re-adjust the pH of the slurry so that it is from about 6.5 to about 8.0, using methods known to those of skill in the art. In some embodiments, the pH of the slurry may be re-adjusted to be about 6.5, about 7.0 or about 8.0.

During or after the first dose of chlorine containing compound is added to the slurry, the slurry may be aerated for a suitable length of time, e.g., up to about 24 hours. Without wishing to be bound by theory, it is believed that aeration of the slurry after a dose of chlorine is added thereto, allows for stabilization of the resulting biological trauma to the microbes contained in the slurry. In some embodiments, aerating the slurry may be accomplished using: an impeller aerator, a venturi pump, a vertical aerator and combinations thereof.

A sample of the slurry is then collected in order to measure for total chlorine residuals. The amount of total chlorine residuals may be expressed in ppm of chlorine. The total chlorine residuals may be measured using any method or means known to one of skill in the art. For example, total chlorine residuals may be measured using a color-wheel test kit, or a digital colorimeter. A digital colorimeter that is useful for measuring total chlorine residuals is the Hach Pocket Colorimeter II (Chlorine Free and Total) from the Hach Company (Loveland, Colo.); this colorimeter may be used to measure total chlorine residuals as follows. DPD tablets, powder or liquid (available from USA BlueBook (Waukegan, Ill.)) are added into a vial of sample water taken from the slurry. The sample is shaken to mix the DPD with the water, which will turn the water pink. The vial is inserted into the colorimeter, which reads the intensity of the color change by emitting a wavelength of light and automatically determining and displaying the color intensity digitally, which reflects the total chlorine residuals. The color measurement range of the colorimeter is from 0 to 4 mg/L, which is equivalent to 0 to 4 ppm of total chlorine residuals.

If the total chlorine residuals in the chlorinated slurry are measured to be less than about 1.5 ppm, then a second dose of a chlorine containing compound is added to the slurry. The slurry may then be aerated for a suitable length of time, e.g., up to another 24 hours, at which point the total chlorine residuals are again measured. In some embodiments, aerating the slurry may be accomplished using: an impeller aerator, a venturi pump, a vertical aerator and combinations thereof. This process may be repeated as needed until the total chlorine residuals are present in a concentration of at least about 1.5 ppm, or at least about 2.0 ppm.

III. Dechlorination of the Slurry

Referencing FIG. 1, Step 3 (300), in embodiments of the method in which the slurry was sterilized through addition of a chlorine containing compound, the slurry is then dechlorinated. Without wishing to be bound by theory, it is believed that dechlorination of a chlorinated slurry may eliminate an environment in the slurry that is not conducive to microbe stability and/or multiplication. In some embodiments, the pH of the slurry is maintained during the dechlorination, whereas in other embodiments, it may be adjusted after dechlorination. In any case, the pH of the slurry may be maintained, or adjusted to, a range of from about 6.5 to about 8.0, using methods known to those of skill in the art. In some embodiments, the pH of the slurry may be maintained at, or adjusted to, about 6.5, about 7.0 or about 8.0 using methods known to those of skill in the art.

Prior to dechlorination of the slurry, it may be transferred for example via gravity feed and/or pumped, to a dechlorination receptacle. In any case, the slurry is dechlorinated using any suitable step that will at least partially, or totally, dissipate the total chlorine residuals from the chlorinated slurry. Suitable methods may be selected from the group of: adding a sulfur containing compound to the chlorinated slurry, exposing the chlorinated slurry to ultraviolet light (e.g., sunlight), aeration and combinations thereof.

In embodiments in which the slurry is dechlorinated by adding a sulfur containing compound, the sulfur containing compound may be selected from the following group of commercially available compounds: sodium bisulfate, potassium bisulfate, sulfur dioxide and combinations thereof. As a general rule of thumb, the chlorinated slurry may be dechlorinated by adding a sulfur containing compound in a molar ratio of about 1:1 with the chlorine containing compound that was previously added in the chlorination step to chlorinate the slurry.

Like in the chlorination of the slurry, dechlorination of the slurry may be achieved by adding one or more doses of a sulfur containing compound to the chlorinated slurry. For example, as described below, dechlorinating the chlorinated slurry may begin with the addition of a first dose of a sulphur containing compound to the chlorinated slurry, and after a given time period, measuring a sample of the slurry for total chlorine residuals.

Once a first dose of sulfur containing compound is added to the chlorinated slurry, the slurry may be aerated a suitable length of time, e.g., up to about 24 hours. Without wishing to be bound by theory, it is believed that aeration of the slurry after a dose of sulfur containing compound is added thereto, drives dissipation of chlorine from the slurry. In some embodiments, aerating the slurry may be accomplished using: an impeller aerator, a venturi pump, a vertical aerator, forced air, diffused air, injected air and combinations thereof. A sample of the slurry is then collected in order to measure for total chlorine residuals.

If greater than 1.0 ppm, greater than 1.2 ppm or greater than 1.5 ppm of total chlorine residuals are present in the sample of water taken from the chlorinated slurry, then a second dose of a sulfur containing compound may be added to the slurry. The slurry may then be aerated for a suitable length of time, e.g., up to about another 24 hours, at which point the total chlorine residuals are again measured. This process may be repeated as needed until the total chlorine residuals are present in a concentration of less than about 1.0 ppm, less than about 0.8 ppm or less than about 0.5 ppm.

IV. Inoculation of the Slurry

Referencing FIG. 1, Step 4 (400), dechlorinated slurry, or sterilized slurry that contains total chlorine residuals of less about 1 ppm, is inoculated with aerobic bacteria. The aerobic bacteria may be selected from: phycophilic bacteria, which thrive at temperatures less than about 50° F., mesophilic bacteria, which thrive at temperatures from about 50° F. to about 105° F., thermophilic bacteria, which thrive at temperatures from about 105° F. to about 150° F., and combinations thereof. In embodiments in which thermophilic bacteria are utilized, then the slurry may be heated. In preferred embodiments, phycophilic and/or mesophilic bacteria are utilized since they may thrive without adding exogenous heat to the slurry.

Any suitable source of aerobic bacteria may be utilized. In some embodiments, the aerobic bacteria may be sourced from commercially available bioaugmentation products. Examples of useful commercial products include Revive NG (which may optionally be used with Revive S) from Bio-Chem. Industries, Inc. (Ooltewah, Tenn.) and Formula D-500 and Bacteria Supplement D500A for Municipal WWTP, each from USA BlueBook (Waukegan, Ill.).

In preferred embodiments, the slurry is moved from the chlorination receptacle to a biological receptacle prior to inoculating the slurry with the aerobic bacteria. In some embodiments, the slurry may be moved from the chlorination receptacle to the biological receptacle via gravity feed and/or pump.

Like in the dechlorination of the slurry, inoculation of the slurry may be achieved by adding one or more doses of aerobic bacteria to the dechlorinated slurry. For example, as described below, inoculating the slurry may begin with the addition of a first dose of aerobic bacteria. If commercially available bioaugmentation products are utilized, the first dose may be determined based upon the supplier's instructions.

Once a first dose of the aerobic bacteria is added to the slurry, the slurry is aerated for a suitable length of time, e.g., up to about 24 hours. In some embodiments, aerating the slurry may be accomplished using: an impeller aerator, a venturi pump, a vertical aerator and combinations thereof. A sample of the slurry may be collected, and using methods known to one skilled in the art, tested to determine whether one or more additional doses of aerobic bacteria should be added to the slurry.

Without wishing to be bound by theory, for the aerobic bacteria to operate properly, the ratio of the food, to the aerobic bacteria, i.e., the "FM ratio," should be optimized. For example, if the FM ratio is too high, the aerobic bacteria will multiply quickly, but may not form a good floc. Conversely, if the FM ratio is too low, there may be a limited amount of food available to the aerobic bacteria and they may lose their motility and clump together, such that a good floc is not formed.

Non-limiting examples of testing methods that may be utilized to determine whether one or more additional doses of aerobic bacteria should be added to the slurry may be selected from the group of measuring: settleability; dissolved oxygen; pH; and combinations thereof.

Settleability, i.e., the settling characteristics of the slurry, may be used to determine the health of the anaerobic bacteria contained therein. Settleability may be measured by one skilled in the art using any suitable method including, but not limited to the "30-minute Settling Test." If the slurry fails the 30-minute settling test, then the aerobic bacteria may not have sufficiently degraded solid materials and/or filamentous materials in the slurry. If the slurry fails the 30-minute settling test, then slurry may be further diluted with water and/or one or more additional doses of aerobic bacteria may be added thereto, and aerated again for a suitable length of time, e.g., up to about another 24 hours.

Measuring the Dissolved Oxygen ("DO") in the slurry may additionally or alternatively be used to determine the health of the aerobic bacteria in the slurry. DO may be measured by one skilled in the art using any suitable method. If the DO of the slurry is below about 1.5, or below about 1.3 or below about 1.0, then one or more additional doses of aerobic bacteria may be added thereto and aerated again for a suitable length of time, e.g., up to about another 24 hours in order to digest additional solids. On the other hand, a DO of above about 1.5, or above about 1.8 or above about 2.0, may indicate that all of the solids have been consumed by the aerobic bacteria and consequently, no additional bacteria need to be added.

Measuring pH of the slurry may additionally or alternatively be used to determine the health of the aerobic bacteria in the slurry. In some embodiments, the aerobic bacteria are healthy (i.e., active) when the slurry has a pH in a given range. In some embodiments, the aerobic bacteria are healthy in a slurry having a pH of from about 6.0 to about 8.0. If the pH of the slurry is above or below the desired range, then one of skill in the art may adjust the pH accordingly.

Once the slurry passes a settleability test, has a desirable DO and/or a desirable pH, then the slurry may be separated into undissolved solids and effluent. In some embodiments, the slurry may pass the 30-minute settling test, have a DO of at least about 1.5 and a pH from about 6.0 to about 8.0, then the slurry may be separated into undissolved solids and effluent.

As compared to the first BOD of the slurry, the BOD of the effluent, i.e., the "second BOD," may be reduced by about 50%, by about 60%, by about 70%, or by about 80%. For land applications, the BOD value of the effluent may have a second BOD of less than about 100 mg/L, less than about 50 mg/L, or less than about 45 mg/L.

Example

Approximately 15 tons of manure are placed in a lagoon having a total surface area of about 80 feet, and an average depth of about 6 feet. The liquid content of the manure is measured and is found to be 75%. Water is added to the manure in a 3:1 ratio and is mixed via continuous aeration to form a slurry using a Kasco® Decorative Display Aerator (¾ hp, 1 ph, 240V) from USA BlueBook (Waukegan, Ill.) at full power.

Once the slurry is obtained, its pH is adjusted to 7.5 with lime. The slurry continues to be aerated as described above.

A sample of the slurry is taken from the lagoon. The BOD value of the slurry is measured using EPA Standard Method 5210 B to be 5,100 mg/L.

10 gallons of 60% sodium hypochloride, available as HTH® liquid chlorinator from Lonza Group Ltd. (Muenchensteinerstrasse 38, Switzerland), is added to the slurry. The slurry is continuously aerated as described above for one hour.

The total chlorine residuals of the slurry are measured as follows. A 5 mL aliquot of the slurry and 5 mL of liquid DPD from USA BlueBook (Waukegan, Ill.) are added into a sample cell for a Hach Pocket Colorimeter II (Chlorine Free and Total); the sample cell and pocket colorimeter are each available from the Hach Company (Loveland, Colo.). The sample cell is shaken by hand for 3 minutes. The sample cell is inserted into the pocket colorimeter, which indicates that the total chlorine residuals in the slurry are present at 1.2 ppm.

Another 10 gallons of the 60% sodium hypochloride, available as HTH® liquid chlorinator from Lonza Group Ltd. (Muenchensteinerstrasse 38, Switzerland), is added to the slurry. The slurry is continuously aerated as described above for another hour. The total chlorine residuals of the slurry are measured, as described above, to be present at 1.8 ppm.

The now chlorinated slurry is transferred via gravity feed to a chlorination lagoon having a total surface area of about 80 feet and an average depth of about 6 feet. The chlorinated slurry continues to be aerated as described above, and its pH is adjusted to 7.5 with lime.

The chlorinated slurry is dechlorinated by adding 20 gallons of liquid sodium bisulfate from USA BlueBook (Waukegan, Ill.) and aerating the slurry as described above for 30 minutes.

The slurry is tested for dechlorination as follows. A 5 mL aliquot of the slurry and 5 mL of liquid DPD from USA BlueBook (Waukegan, Ill.) are added into a sample cell for a Hach Pocket Colorimeter II (Chlorine Free and Total); the sample cell and pocket colorimeter are each available from the Hach Company (Loveland, Colo.). The sample cell is shaken by hand for 3 minutes. The sample cell is inserted into the pocket colorimeter, which indicates that the total chlorine residuals in the slurry are present at 0 ppm.

The dechlorinated slurry is transferred via gravity feed to a biological lagoon having a total surface area of about 80 feet and an average depth of about 6 feet. The dechlorinated slurry continues to be aerated as described above, and its pH is adjusted to 7.5 with lime.

The slurry is inoculated by adding one gallon each of Revive NG and Revive S from Bio-Chem Industries, Inc. (Ooltewah, Tenn.) per million gallons of slurry. The slurry is aerated 24 hours as described above.

A sample of the inoculated slurry is measured for its BOD value using the 5 Day BOD method. The BOD of the slurry is found to be about 2,200 mg/L.

The slurry is re-inoculated by adding 25 pounds of each of Revive NG and Revive S from Bio-Chem Industries, Inc. (Ooltewah, Tenn.). The slurry is aerated 24 hours as described above.

A sample of the inoculated slurry is measured for its BOD value using EPA Standard Method 5210 B method. The BOD of the slurry is found to be 45 mg/L.

Since the BOD of the inoculated slurry is below 100 mg/L, it may safely be applied to farmland without the risk of contaminating the ground water. Before applying the inoculated slurry to the farmland it is separated into undissolved solids and effluent by clarification settling. The undissolved solids are applied to the farmland and the effluent is subsequently utilized for irrigation or other uses.

What is claimed is:

1. A sanitary waste treatment method comprising the steps of:
   a. adding water to the sanitary waste to form a slurry characterized by a first biochemical oxygen demand;
   b. aerating the slurry;
   c. chlorinating the slurry to produce a sterilized slurry;
   d. dechlorinating the sterilized slurry to produce a dechlorinated slurry;
   e. inoculating the dechlorinated slurry with aerobic bacteria, wherein the aerobic bacteria digest solid waste in the slurry.

2. The sanitary waste treatment method of claim 1, further comprising the step of mixing the slurry.

3. The sanitary waste treatment method of claim 1, further comprising the step of separating the slurry into undigested solids and effluent.

4. The sanitary waste treatment method of claim 3, wherein the effluent is characterized by a second biochemical oxygen demand that is at least about 50% less than the first biochemical oxygen demand.

5. The sanitary waste treatment method of claim 1, wherein the step of chlorinating the slurry kills at least about 95% of microbes contained in the slurry.

6. The sanitary waste treatment method of claim 1, wherein the dechlorination of the slurry comprises the step of adding a sulfur containing compound to the slurry.

7. The sanitary waste treatment method of claim 1, wherein the slurry is aerated during steps a, c, d and e.

8. The sanitary waste treatment method of claim 1, wherein the slurry is maintained at a pH of from about 6.5 to about 8.0 during steps a through e.

9. The sanitary waste treatment method of claim 1, wherein the aerobic bacteria are selected from the group consisting of phycophilic bacteria, mesophilic bacteria and combinations thereof.

10. The sanitary waste treatment method of claim 1, wherein the aerobic bacteria are thermophilic bacteria and further comprising the step of heating the slurry.

11. A sanitary waste treatment method comprising the steps of:
   a. sterilizing a slurry containing sanitary waste by adding chlorine to the slurry until the slurry contains total chlorine residuals of at least about 1.5 parts per million;
   b. dechlorinating the slurry by adding a sulfur containing compound to the slurry;
   c. inoculating the slurry with aerobic bacteria;
   d. digesting sanitary waste in the slurry with the bacteria;
   e. aerating the slurry during steps a through d; and
   f. separating the slurry into undigested solid waste and effluent.

12. The sanitary waste treatment method of claim 11, wherein steps a through e reduce the biochemical oxygen demand of the slurry by at least about 50%.

13. The sanitary waste treatment method of claim 11, wherein steps a through e reduce the biochemical oxygen demand of the slurry by at least about 80%.

14. The sanitary waste treatment method of claim 11, wherein chlorine is added to the slurry at a concentration of at least about 5 parts per million.

15. The sanitary waste treatment method of claim 11, wherein the chlorine is added to the slurry at a concentration of at least about 10 parts per million.

16. The sanitary waste treatment method of claim 11, further comprising the step of forming the slurry by adding water to the sanitary waste.

17. The sanitary waste treatment method of claim 11, wherein the slurry has a total liquid content of from about 75% to about 95%.

18. The sanitary waste treatment method of claim 11, wherein the slurry is aerated using a device selected from the group of: an impeller aerator; a venturi pump; a vertical aerator; and combinations thereof.

19. A sanitary waste treatment method comprising the steps of:
   a. placing slurry comprising sanitary waste and water in a holding receptacle;
   b. sterilizing the slurry by at least about 95% by adding chlorine to the slurry;
   c. moving the sterilized slurry into a dechlorination receptacle;
   d. dechlorinating the slurry by adding a sulfur containing compound to the slurry;
   e. moving the dechlorinated slurry into a biological receptacle;
   f. inoculating the slurry with aerobic bacteria;
   g. digesting solid waste in the slurry with the aerobic bacteria;
   h. separating the slurry into undigested solid waste and supernatant; and
   i. aerating the slurry during steps b, d, f and g.

20. The sanitary waste treatment method of claim 19 further comprising the step of maintaining the slurry at a pH of about 6.5 and about 8.0 during steps b through g.

* * * * *